(12) United States Patent
Chow

(10) Patent No.: US 6,167,910 B1
(45) Date of Patent: Jan. 2, 2001

(54) MULTI-LAYER MICROFLUIDIC DEVICES

(75) Inventor: Calvin Y. H. Chow, Portola Valley, CA (US)

(73) Assignee: Caliper Technologies Corp., Mountain View, CA (US)

( * ) Notice: Under 35 U.S.C. 154(b), the term of this patent shall be extended for 0 days.

(21) Appl. No.: 09/231,209

(22) Filed: Jan. 14, 1999

Related U.S. Application Data

(60) Provisional application No. 60/072,001, filed on Jan. 20, 1998.

(51) Int. Cl.$^7$ .................................................. F15C 1/04

(52) U.S. Cl. ............................ 137/827; 137/526; 137/559

(58) Field of Search .......................... 137/526, 826, 137/833, 559; 251/129.01

(56) References Cited

U.S. PATENT DOCUMENTS

| | | | | |
|---|---|---|---|---|
| 3,468,331 | * | 9/1969 | O'Neal ................................. | 137/833 |
| 3,495,604 | * | 2/1970 | Trask ................................... | 137/833 |
| 3,495,608 | * | 2/1970 | O'Keefe ............................... | 137/833 |
| 3,528,445 | * | 9/1970 | Shinn et al. .......................... | 137/833 |
| 3,534,757 | * | 10/1970 | Doherty ............................... | 137/833 |
| 3,548,849 | * | 12/1970 | Purcell ................................. | 137/833 |
| 3,587,614 | * | 6/1971 | Burke ................................... | 137/833 |
| 3,587,615 | * | 6/1971 | Thomson ............................. | 137/833 |
| 3,658,088 | * | 4/1972 | Jensen et al. ..................... | 137/561 R |
| 3,731,700 | * | 5/1973 | Cohen .................................. | 137/833 |
| 3,747,628 | * | 7/1973 | Holster et al. ....................... | 137/269 |
| 3,811,474 | * | 5/1974 | Bauer et al. ......................... | 137/833 |
| 3,942,558 | * | 3/1976 | Honda .................................. | 137/833 |
| 4,390,403 | | 6/1983 | Batchelder . | |
| 4,729,403 | * | 3/1988 | Roche .................................. | 137/559 |
| 4,908,112 | | 3/1990 | Pace . | |
| 4,949,755 | * | 8/1990 | Thurston et al. ..................... | 137/833 |
| 5,126,022 | | 6/1992 | Soane et al. . | |
| 5,417,235 | * | 5/1995 | Wise et al. ................................ | 137/1 |
| 5,498,392 | | 3/1996 | Wilding et al. . | |
| 5,571,410 | | 11/1996 | Swedberg et al. . | |

(List continued on next page.)

FOREIGN PATENT DOCUMENTS

| | | |
|---|---|---|
| WO 9604547 | 2/1996 | (WO) . |
| WO 9702357 | 1/1997 | (WO) . |

OTHER PUBLICATIONS

Dasgupta, P.K. et al., "Electroosmosis: A Reliable Fluid Propulsion System for Flow Injection Analysis," *Anal. Chem.* 66:1792–1798 (1994).

Jacobson, S.C. et al., "Fused Quartz Substrates for Microchip Electrophoresis," *Anal. Chem.* 67:2059–2063 (1995).

Manz, A. et al., "Electroosmotic pumping and electrophoretic separations for miniaturized chemical analysis systems," *J. Micromech. Microeng.* 4:257–265 (1994).

Ramsey, J.M. et al., "Microfabricated chemical measurement systems," *Nature Med.* 1:1093–1096 (1995).

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow Within a Manifold of Capillaries on a Glass Chip," *Anal. Chem.* 66:3485–3491 (1994).

*Primary Examiner*—A. Michael Chambers
*Assistant Examiner*—Thomas L. McShane
(74) *Attorney, Agent, or Firm*—Matthew B. Murphy

(57) ABSTRACT

The present invention provides multi-layer microfluidic systems, by providing additional substrate layers, e.g., third, fourth, fifth and more substrate layers, mated with the typically described first and second layers. Microfabricated elements, e.g., grooves, wells and the like, are manufactured into the surfaces between the various substrate layers. These microfabricated elements define the various microfluidic aspects or structures of the overall device, e.g., channels, chambers and the like. In preferred aspects, a separate microscale channel network is provided between each of the substrate layers.

39 Claims, 3 Drawing Sheets

U.S. PATENT DOCUMENTS

| | | |
|---|---|---|
| 5,585,069 | 12/1996 | Zanzucchi et al. . |
| 5,593,838 | 1/1997 | Zanzucchi et al. . |
| 5,603,351 | 2/1997 | Cherukuri et al. . |
| 5,635,358 | 6/1997 | Wilding et al. . |
| 5,637,469 | 6/1997 | Wilding et al. . |
| 5,681,484 | 10/1997 | Zanzucchi et al. . |
| 5,699,157 | 12/1997 | Parce . |
| 5,750,015 | 5/1998 | Soane et al. . |
| 5,779,868 | 7/1998 | Parce et al. . |
| 5,800,690 | 9/1998 | Chow et al. . |
| 5,842,787 | 12/1998 | Kopf-Sill et al. . |
| 5,852,495 | 12/1998 | Parce . |
| 5,869,004 | 2/1999 | Parce et al. . |
| 5,876,675 | 3/1999 | Kennedy . |
| 5,880,071 | 3/1999 | Parce et al. . |

* cited by examiner

MULTI-LAYER MICROFLUIDIC DEVICES

CROSS REFERENCE TO RELATED APPLICATION

This application claims priority from U.S. Provisional Patent Application Ser. No. 60/072,001, filed Jan. 20, 1998, which is hereby incorporated herein by reference in its entirety for all purposes.

BACKGROUND OF THE INVENTION

Microfluidic devices and systems have been gaining increasing interest for their ability to provide improved methods of performing chemical, biochemical and biological analysis and synthesis. In particular, the small size and automatability of these microfluidic systems provides a variety of advantages in terms of low reagent requirements, low space requirements, shorter reaction times, and integratability. All of these advantages together, provide systems which can be extremely useful in performing large numbers of reactions in parallel, in order to provide enhanced analytical throughput.

In general, the production of microfluidic devices has been enabled by advancements in microfabrication technology used in the electronics and semiconductor manufacturing industries. Specifically, technologies, such as photolithography, wet chemical etching, injection molding of plastics, and the like, have been used to fabricate microscale channels and wells in the surface of planar substrates. Overlaying a second planar substrate on the surface of the first creates the microfluidic channels and chambers of the device. While these microfabrication techniques permit the incorporation of relatively complex channel networks in a relatively small area, the ability to further reduce the size of microfluidic devices produced in this manner has been somewhat limited by the two dimensional orientation of the channel networks. Specifically, because channel networks have been generally defined in two dimensions, e.g., in a single layer, different channel networks could not cross or otherwise occupy the same area on the substrate.

In order to allow further reduction of microfluidic device size, it would therefore be desirable to provide microfluidic devices that are not limited by the two-dimensional nature of typical microfluidic devices. The present invention meets these and other needs.

SUMMARY OF THE INVENTION

The present invention generally overcomes the limits of two-dimensional microfluidic systems by providing multi-layer microfluidic devices and systems (e.g., 3-dimensional).

In one aspect, the present invention provides microfluidic devices which comprise a body structure having at least first, second and third substrate layers, the second substrate layer disposed on top of the first substrate layer and the third substrate layer disposed on top of the second substrate layer. The devices include at least first, second and third ports disposed in the body structure. The devices of the invention also include at least first and second microscale channel networks. The first channel network is typically disposed between the first and second substrate layers, and is in fluid communication with the first and second ports, but not the third port. The second channel network, on the other hand, is disposed between the second and third layers, and is in fluid communication with the first and third ports, but not the second port.

The present invention also includes systems incorporating these microfluidic devices, which systems typically include a material transport system operably linked to each of the first, second and third ports of the device, for selectively controlling movement of material in the first and second channel networks.

In a related aspect, the present invention provides a microfluidic device comprises at least three substrate layers and at least two channel networks, as described above. However, in this aspect, the device includes at least one fluid passage disposed through the second substrate layer, which provides fluid communication between the first channel network and the second channel network.

In another aspect, the present invention provides methods of performing a plurality of different analyses on a single fluid sample. The methods comprise providing a microfluidic device according to the invention, e.g., as described above. The fluid sample to be analyzed is placed into the first, common port of the device. The sample is then transported through each of the first and second channel networks, whereby a different reaction or analysis is performed on the sample in each of the channel networks. The result of these different reactions or analyses are then detected.

In a more specific embodiment, the multi-layer devices of the invention are useful in methods of sequencing nucleic acids. In particular, the devices for this application typically include at least five substrate layers. The devices also include at least four separation channels, each of the separation channels disposed between two different substrate layers. A common sample reservoir is included, connected to each of the four separation channels via four separate sample introduction channels. Four reagent channels are also provided, wherein each reagent channel independently connects each of the four sample introduction channels with a separate one of four separate reagent reservoirs disposed in the body structure. Each of the four separate reagent reservoirs comprise a different reagent mixture of nucleotide triphosphates, primer sequences, nucleic acid polymerases, and a separate dideoxynucleotide.

In a related aspect, the present invention provides methods of sequencing nucleic acids using the devices described above. Specifically, the target nucleic acid is separately combined with each of the four different reagent mixtures in each of the four sample introduction channels. The products of the reaction resulting from this combination are then injected into the separation channel to size the different products. Based upon the size of the reaction products, one can determine the sequence of nucleotides in the target nucleic acid sequence.

BRIEF DESCRIPTION OF THE FIGURES

FIG. 1 illustrates an embodiment of a multi-layer device.

DETAILED DESCRIPTION OF THE INVENTION

Figure 1A:
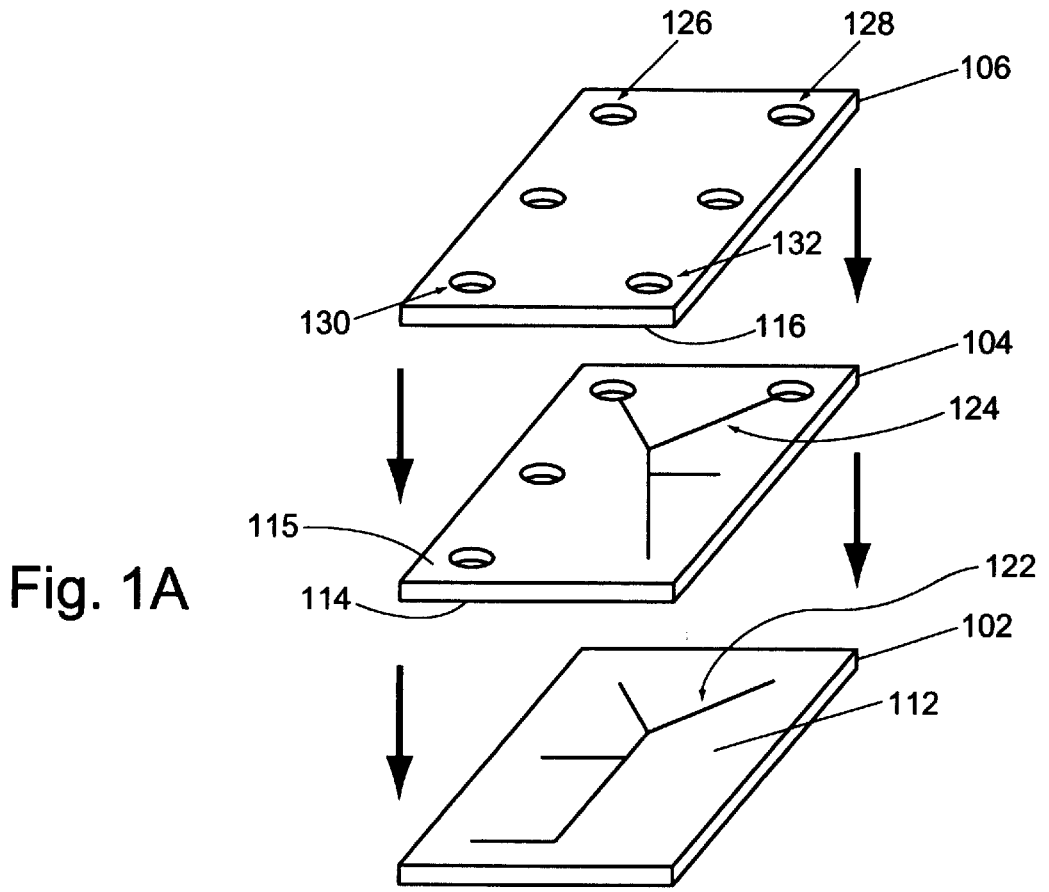
FIG. 1A illustrates the multi-layer construction of the device from a perspective view.

In most instances, microfluidic devices have been manufactured using microfabrication methods commonly employed in the electronics industry. Such methods generally involve the fabrication of microscale structures, e.g., grooves, wells, depressions and the like, on the upper planar surface of a first solid substrate material. A second substrate layer having a lower planar surface is then bonded over this surface, which covers and seals the grooves and wells to form the channels and chambers. As a result of these manufacturing techniques, microfluidic devices most often employ a planar structure where, aside from their intrinsic depth, the fluidic elements generally exist in two dimensions. The present invention, on the other hand, provides three dimensional microfluidic devices, e.g., employing multi-layered channel structures and networks. By providing multiple layers, the present invention provides a large number of advantages over previously described systems. For example, by providing multi-layered devices and systems, the present invention substantially expands the amount of parallelization that can be achieved using microfluidic systems. Furthermore, by taking advantage of both surfaces of planar substrates, the present invention also permits the optimal use of substrate materials, allowing further miniaturization of fluidic processes, as well as providing cost advantages in terms of substrate conservation. Finally, in the case of some types of microfluidic systems, such as electrokinetic based microfluidic systems, these multi-layer devices permit the simultaneous use of individual electrode interfaces on multiple layers of the device, thereby simplifying electrical control of such devices.

I. Multi-layer Devices

Generally, the present invention provides multi-layer microfluidic systems, by providing additional substrate layers, e.g., third, fourth, fifth and more substrate layers, mated with the typically described first and second layers. Microfabricated elements, e.g., grooves, wells and the like, are manufactured into the surfaces between the various substrate layers. These microfabricated elements define the various microfluidic aspects or structures of the overall device, e.g., channels, chambers and the like. In preferred aspects, a separate microscale channel network is provided between each of the substrate layers.

As used herein, the term "microscale" or "microfabricated" generally refers to structural elements or features of a device which have at least one fabricated dimension in the range of from about 0.1 μm to about 500 μm. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 μm, and typically between about 0.1 μm and about 500 μm. In the devices of the present invention, the microscale channels or chambers preferably have at least one cross-sectional dimension between about 0.1 μm and 200 μm, more preferably between about 0.1 μm and 100 μm, and often between about 0.1 μm and 20 μm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of more than two separate substrate layers which when appropriately mated or joined together, form the microfluidic device of the invention, e.g., containing the multiple channel networks described herein. Typically, the microfluidic devices described herein will comprise at least three substrate layers, including a bottom substrate layer, a middle substrate layer and a top substrate layer. In some aspects the microfluidic devices of the present invention will include more than four, five, six, seven eight or more substrate layers, depending upon the nature of the operation for which the device is to be used.

As used herein, the terms "substrate" or "substrate layer" are used interchangeably to refer to solid planar substrates having first and second opposing, or substantially parallel, planar surfaces. A variety of substrate materials may be employed as the various layers of the device. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Substrates are also generally selected for their electrokinetic properties, e.g., surface potential, thermal and optical properties, e.g., transparency etc. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLONTM), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. No. 5,885,470, and which is incorporated herein by reference in its entirety for all purposes.

As noted above, the various substrate layers of the microfluidic devices are mated or bonded together to form the microfluidic elements of the device. Bonding of substrate layers is generally carried out under any of a number of methods or conditions known in the art. Conditions under which substrates may be bonded together are generally widely understood, and such bonding of substrates is generally carried out by any of a number of methods, which may vary depending upon the nature of the substrate materials used. For example, thermal bonding of substrates may be applied to a number of substrate materials, including, e.g., glass or silica based substrates, as well as polymer based substrates. Such thermal bonding typically comprises mating together the substrates that are to be bonded, under conditions of elevated temperature and, in some cases, application of external pressure. The precise temperatures and pressures will generally vary depending upon the nature of the substrate materials used.

For example, for silica-based substrate materials, i.e., glass (borosilicate glass, Pyrex™, soda lime glass, etc.), quartz, and the like, thermal bonding of substrates is typically carried out by pressing the substrates together at temperatures ranging from about 500° C. to about 1400° C., and preferably, from about 500° C. to about 1200° C. For example, soda lime glass is typically bonded at temperatures around 550° C., whereas borosilicate glass typically is thermally bonded at or near 800° C. Quartz substrates, on the other hand, are typically thermally bonded at temperatures at or near 1200° C. These bonding temperatures are typically achieved by placing the substrates to be bonded into high temperature annealing ovens. These ovens are generally commercially available from, e.g., Fischer Scientific, Inc., and LabLine, Inc.

Polymeric substrates that are thermally bonded on the other hand, will typically utilize lower temperatures and/or pressures than silica-based substrates, in order to prevent excessive melting of the substrates and/or distortion, e.g., flattening of the interior portion of the device, i.e., channels or chambers. Generally, such elevated temperatures for bonding polymeric substrates will vary from about 80° C. to about 200° C., depending upon the polymeric material used, and will preferably be between about 90° C. and 150° C. Because of the significantly reduced temperatures required for bonding polymeric substrates, such bonding may typically be carried out without the need for high temperature ovens, as used in the bonding of silica-based substrates.

Adhesives may also be used to bond substrates together according to well known methods, which typically comprise applying a layer of adhesive between the substrates that are to be bonded and pressing them together until the adhesive sets. A variety of adhesives may be used in accordance with these methods, including, e.g., UV curable adhesives, that are commercially available. Alternative methods may also be used to bond substrates together in accordance with the present invention, including e.g., acoustic or ultrasonic welding, RF welding and/or solvent welding of polymeric parts.

As used herein, the term "channel network" refers to one or more microscale channels that are disposed between two substrates. In preferred aspects, such channel networks include at least two microscale channels, and preferably, at least two intersecting microscale channels. The intersection of channels can include channels which intersect and cross, e.g., at "four-way intersections, as well as a channel intersection wherein one channel intersects and terminates in another channel, e.g., at a "T" or "three-way" intersection. In many aspects, the individual channel networks will preferably include at least three intersecting channels, in some aspects, greater than four intersecting channels and often greater than five, six or even eight intersecting channels.

Typically included within a given channel network are channels in which the desired analysis is to take place, or "analysis channels." Also, typically included are channels for delivering reagents, buffers, diluents, sample material and the like to the analysis channels. Analysis channels optionally include separation matrices disposed within, for separating/fractionating materials transported down the length of these channels, for analysis, i.e., size or charged based fractionation of materials, e.g., nucleic acids, proteins etc. Suitable separation matrices include, e.g., GeneScan™ polymers (Perkin Elmer-Applied Biosystems Division, Foster City, Calif.). Alternatively, analysis channels are devoid of any separation matrix, and instead, merely provide a channel within which an interaction, reaction etc., takes place. Examples of microfluidic devices incorporating such analysis channels arc described in, e.g., Published PCT Application No. WO 98/00231, and U.S. Pat. No. 5,976,336, each of which is hereby incorporated herein by reference in its entirety for all purposes.

One of the advantages of the present invention is to provide microfluidic devices that make optimal use of the substrate material from which they are fabricated. As such, in preferred aspects, the channel networks used in the devices of the present invention will typically exist in a limited space. Specifically, the channel networks will typically be entirely incorporated in a substrate area that is less than 3 cm$^2$. In particularly preferred aspects, the entire channel network will be incorporated in an area of less than 1 cm$^2$. Often, the entire channel network will be incorporated in less than 0.5 cm$^1$. In order to ensure that the channel networks are incorporated within the preferred range of areas, any given straight portion of any channel of the device will typically have a length that is less than 1 cm, preferably, less than 0.8 cm, and in many cases, less than 0.5 cm. Specific channels may have overall lengths far greater than these lengths where those channels include serpentine or other turning or more complex geometries.

Figure 1B:
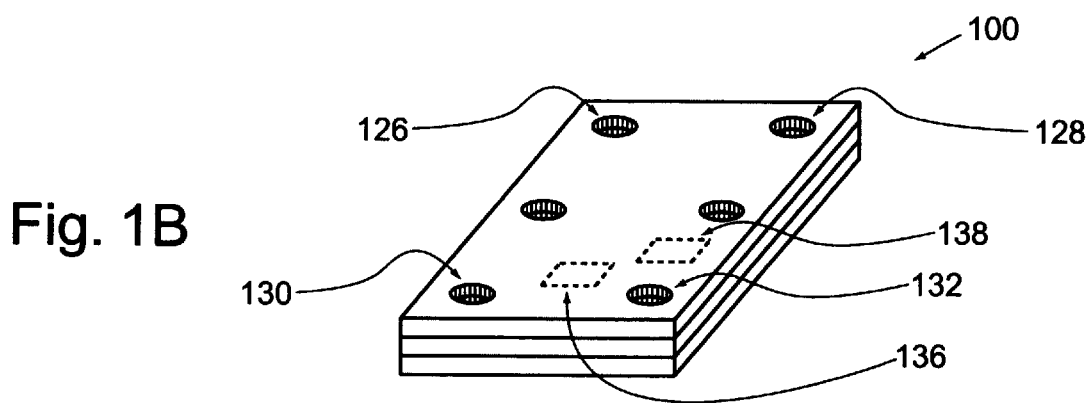
FIG. 1B illustrates a perspective view of an assembled multi-layer device.
Figure 1C:
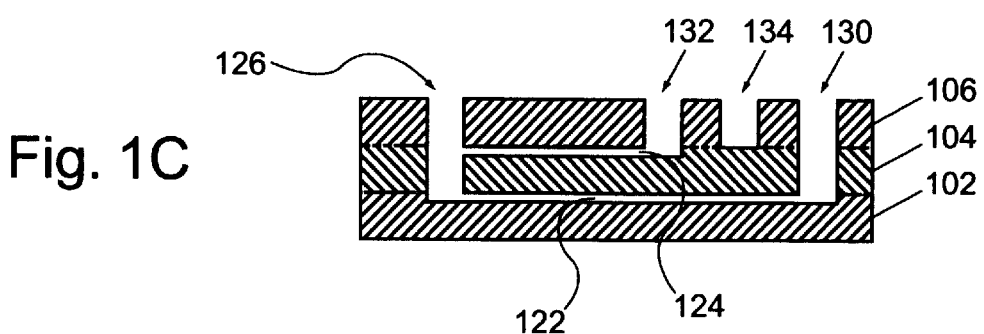
FIG. 1C illustrates a side view of a multi-layered microfluidic device.

An example of a multi-layer microfluidic device according to the present invention is schematically illustrated in FIG. 1. FIG. 1A illustrates the three-layer construction of the device from a perspective view. FIG. 1B illustrates a perspective view of an assembled device, e.g., where the layers are mated together. FIG. 1C illustrates a side view of the assembled device. As shown, the device 100 includes multiple substrate layers, such as bottom substrate 102, middle substrate 104 and top substrate 106. Bottom substrate 102 includes a top surface 112, which is mated with the bottom surface 114 of the middle substrate 104. The top surface 115 of the middle substrate 104 is likewise mated with the bottom surface 116 of the top substrate 106. A first channel network 122 is fabricated into the top surface 112 of the bottom substrate 102, as a series of grooves. A similar series of grooves is fabricated into the top surface 115 of the middle substrate 104, to form a second channel network 124. Upon mating the top surface of the bottom substrate with the bottom surface of the middle substrate, these grooves form the channels of the device. Alternatively, the channel network 122 is optionally fabricated onto the bottom surface of middle substrate 104. Upon mating with bottom substrate 102, the channels of the device are formed. This alternate method provides for cost savings where materials for the substrate incorporating the channel networks are substantially more costly than those substrates used as cover layers. Further, alignment of channel networks on different layers of the device is made more simple by their fabrication on a single substrate.

A plurality of ports is also provided through the substrate layers of the device, to provide access to the channel networks. In the devices of the present invention, each of the channel networks of the device is in fluid communication with at least two ports or reservoirs disposed in the body of the device. In preferred aspects, at least one port is common to, i.e., in simultaneous fluid communication with, two or more channel networks, while at least one port is typically specific to a single channel network.

In order to be common to multiple channel networks in the multi-layered devices of the invention, a port must traverse multiple substrate layers. An example of this port structure is illustrated in FIGS. 1A–C. For example, ports 126 and 128 are shown in FIGS. 1A and 1C, as apertures disposed through upper substrate 106 and middle substrate 104, providing access to and fluid communication with both channel network 124 and channel network 122. Meanwhile, port 132 is shown disposed through only the top substrate 106, whereupon it is in fluid communication only with channel network 124. Port 130, on the other hand is disposed through top substrate 106 and middle substrate 104, but oriented at a position in the substrate such that it only provides access to, and is in fluid communication with only channel network 122. This is a result of channel network 124 not extending to and intersecting port 130. A schematic illustration of this type of port structure is shown in FIG. 1C, from a side view.

In some instances, the ports of the device, common or otherwise, may be disposed through all of the layers of the device. For example, with reference to the devices illustrated in FIGS. 1A, 1B and 1C, ports 126, 128 and 130 can optionally be disposed through bottom substrate 102, in addition to being disposed through middle and top substrates 104 and 106, respectively. Such port structures are particularly useful where extremely small fluid volumes are to be introduced into device, requiring small diameter ports. Specifically, small diameter ports having a closed end can result in the trapping of bubbles below a volume of fluid that is placed into the port, due to surface tension effects of the fluid. However, by providing a port having an open bottom, there is provided an escape route for the bubbles. Additionally, the fluid introduced into the port is maintained within the port by virtue of the capillary forces exerted by the walls of the port. This type of port structure is described in substantial detail in commonly owned U.S. patent application Ser. No. 08/870,944, filed Jun. 6, 1997, and incorporated herein by reference.

In addition to providing fluid access and/or storage for the channel networks of the device, the ports of the device also typically provide access for the material direction and transport systems, which move and direct materials and/or fluids through the various channel networks of the device. Such fluid direction and transport systems typically include, e.g., micromechanical systems employing micropumps and microvalves, pressure based and/or pneumatic systems which move and direct materials by application of pressure differentials across channels, electrokinetic material transport systems which move materials by applying electric fields across channel lengths, and the like.

Pressure based material transport systems typically operate by applying a pressure differentials from one end of a channel through which material movement is desired, to the other end of the channel. By applying appropriate pressures across intersecting channels, one can control material direction through the intersections of channels, and in and out of chambers (see, e.g., Published PCT Application No WO 97/02357. Typically, controlled pressures are applied to the ports of the microfluidic device, which ports are in communication with the channel networks.

In particularly preferred aspects, the devices and systems of the present invention utilize electrokinetic material transport and direction systems. "Electrokinetic material transport and direction systems," as described herein, include systems which transport and direct materials within an interconnected channel and/or chamber containing structure, through the application of electrical fields to the materials. Application of this electric field causes material movement through and among the channels and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. In particularly preferred aspects, however, the electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547 to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic flow of this material across the intersection could be accomplished by applying a voltage gradient across the length of the horizontal channel, i.e., applying a first voltage to the left terminus of this channel, and a second, lower voltage to the right terminus of this channel, or by grounding that terminus. However, this type of material flow through the intersection results in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

The above described microfluidic devices provide enhanced ability to perform parallel analyses on a single material placed into a single microfluidic device, i.e., serial or single to parallel conversion. However, the multi-layer microfluidic devices of the present invention also permit greater freedom in constructing channel networks. Specifically, such multi-layer devices include channels or channel networks that bridge other channels or channel networks, by detouring from one layer of the device to the other. Thus, in addition to providing multi-layer microfluidic devices wherein channel networks on different layers are in fluid communication via common ports, the present invention also provides devices that include fluid passages disposed through substrates, in order to provide fluid communication between channels or channel networks that are disposed on different layers of the device. By permitting such cross-over channel structures, the present invention provides greater freedom in designing channel networks, as well as greater channel density per unit area of substrate. An example of a cross over channel structure in a multi-layer device is shown in FIG. 3.

Figure 3A:
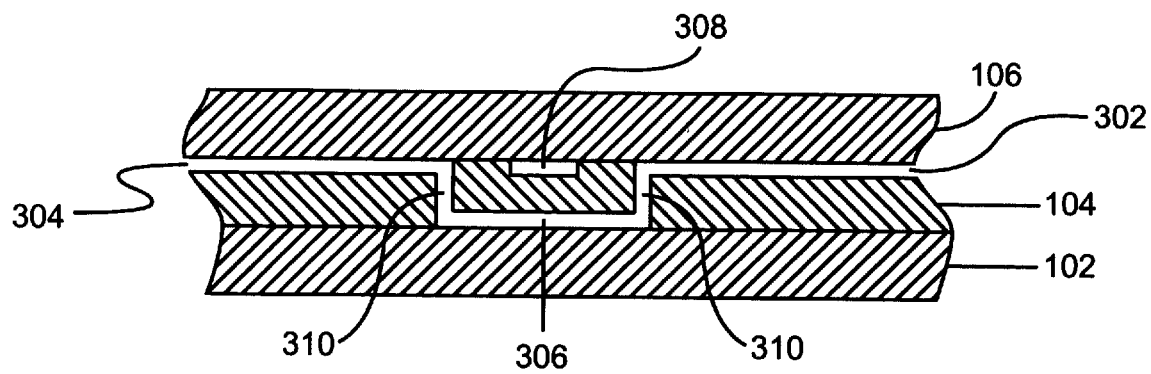
FIG. 3 illustrates an alternate embodiment of a multi-layer microfluidic device incorporating cross-over channels.
Figure 3B:
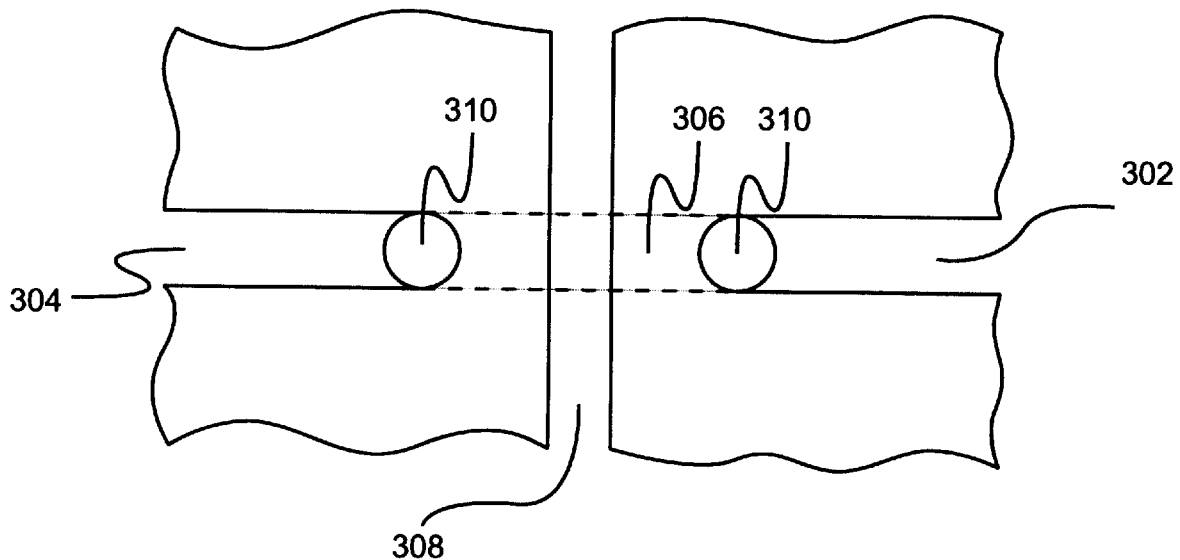

FIGS. 3A and 3B illustrate a portion of a multi-layer microfluidic device. The device is again fabricated from a bottom substrate 102, middle substrate 104 and top substrate 106. The device portion is illustrated from a side view (FIG. 3A) and a top view (FIG. 3B). The device includes channels 302, 304, 306 and 308 (channel 308 is shown from the end view) fabricated into the upper surface of the middle substrate 104. Channel 302 is in fluid communication with channel 304 via channel 306 which, as shown, is fabricated into the bottom surface of the middle substrate 104. Each of channels 302 and 304 communicates with channel 306 via a passage 310 fabricated through the middle substrate layer. These fluid passages 310 are generally fabricated using the same methods used in producing the port structures described with reference to FIG. 1. For example, microscale drills, air abrasion, laser ablation and like methods are readily applicable to fabricating these passages through the substrates. Further, for thinner substrate materials, chemical etching techniques are also useful in fabricating these passages.

Because these passages are intended for fluid transport, rather than fluid introduction, i.e., as in the case of the ports described with reference to FIG. 1, they will generally have a substantially smaller diameter. Specifically, in the microfluidic systems described herein, it is generally advantageous to minimize any dead volumes within the device to avoid negating any advantages otherwise gained in low volume or high throughput processing. For example, the ports described above will generally range from about 0.5 mm to about 10 mm, and preferably from about 1 mm to about 5 mm, the fluid passages disposed through the substrates on the other hand, will typically range from about 30 $\mu$m to about 500 $\mu$m in diameter, and preferably will be fabricated to a similar cross section as the channels with which the passages communicate. Again, as with the devices illustrated in FIG. 1, the device partially shown in FIG. 3 also typically includes ports in communication with the channels of the device (ports not shown). Material direction and transport is also preferably accomplished using controlled electrokinetic transport methods, as described above.

II. Instrumentation

The systems described herein generally include microfluidic devices, as described above, in conjunction with additional instrumentation. The additional instrumentation typically includes power supplies and controllers, for controlling fluid transport and direction within the devices, as described in greater detail below. The instrumentation also typically includes detection instrumentation for detecting or sensing results of the operations performed by the system. Further, the instrumentation often includes processor instrumentation, e.g., computers etc., for instructing the controlling instrumentation in accordance with preprogrammed instructions, receiving data from the detection instrumentation, and for analyzing, storing and interpreting the data, and providing the data and interpretations in a readily accessible reporting format.

A variety of controlling instrumentation may be utilized in conjunction with the microfluidic devices described above, for controlling the transport and direction of fluids and/or materials within the devices of the present invention, in accordance with the systems described above. Typically, such controllers incorporate the driving system for the material transport system, 1.5 e.g., electrical power sources, pressure sources etc. The controller also typically includes an appropriate interface component, for interfacing the microfluidic device with he transport driving system, e.g., power source, pressure source, etc. As noted above, the systems described herein preferably utilize electrokinetic material direction and transport systems. As such, the controller systems for use in conjunction with the microfluidic devices typically include an electrical power supply and circuitry for concurrently delivering appropriate voltages to a plurality of electrodes that are placed in electrical contact with the fluids contained within the microfluidic devices via the ports described above. Examples of particularly preferred electrical controllers include those described in, e.g., Published PCT Application No. WO 98/00707, the disclosure of which is hereby incorporated herein by reference in their entirety for all purposes. In brief, the controller uses controlled electric current or power to control material transport the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes o f the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system.

In the microfluidic systems described herein, a variety of detection methods and systems may be employed, depending upon the specific operation that is being performed by the system. Often, a microfluidic system will employ multiple different detection systems for monitoring the output of the system. Examples of detection systems include optical sensors, temperature sensors, electrochemical sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber.

The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material.

The detector may exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer. Additionally, the detector and/or the device will typically include an interface element for placing the detector in sensory communication with a channel of the device. In the case of potentiometric detection systems, such interface components typically include electrical couplings on the detector and device, for connecting the sensor portion of the device to the detector portion of the controller. Alternatively, the interface component can include thin regions of the device's body structure which when the device is mounted on the controller, place the detector in sensory communication with the channels of the device, e.g., to measure temperature or some optical property within a channel.

In preferred aspects, the devices of the present invention typically include one or more detection windows, for detecting the progress and/or results of a particular operation being performed within the device. As used herein, the term "detection window" refers to a region on the body of a microfluidic device that is capable of transmitting a detectable signal from one or more microfluidic channels of the device to the exterior of the device, where it can be readily detected, e.g., by a detector disposed adjacent the detection window. FIG. 1B illustrates the orientation of these detection windows 136 and 138, on the body of the device 100 which incorporates two separate channel networks, and consequently, two detection windows 136 and 138. Although it is preferred to have separate detection windows for separate channel structures, it is not required. For example, a single detection window is used where two channel networks overlay each other, or are in close proximity to each other, but produce readily distinguishable signals, such as different signal types, e.g., light vs. radiation, emitted fluorescence at different wavelengths, and the like. In preferred aspects, the detection windows are optical detection widows, permitting the transmission of an optical signal from one or more channels or channel networks to the exterior of the device, for detection by an appropriately positioned optical detector.

Figure 2:
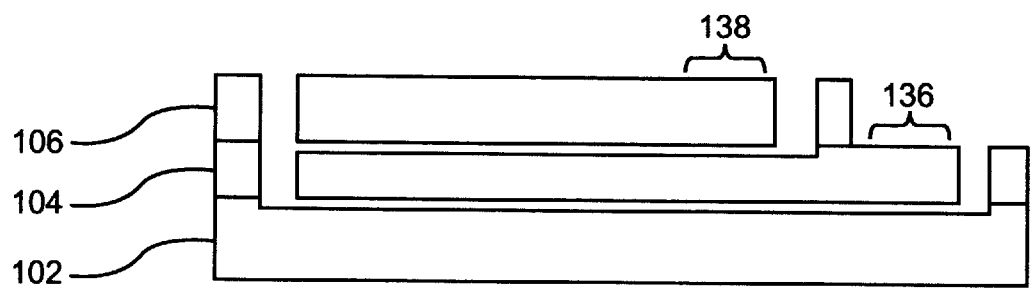
FIG. 2 illustrates an embodiment of a microfluidic device incorporating an alternate detection window structure.

In the case of multi-layer devices, some of the channel networks may include multiple substrate layers between the channel and the detector. Although selection of highly pure substrate materials can reduce the amount of interference caused by these thicker substrates, e.g., autofluorescence and the like, as well as increase light collection efficiencies, it is generally desirable to minimize the number of substrate layers or amount of substrate material between the channel network and the detector, at the detection window. Generally, this is accomplished by providing windows or apertures through the upper substrate layers so as to minimize the number of substrate layers through which the signal must pass in order to reach the detector. One example of this detection window structure is shown in FIG. 1C, which illustrates a detection window for the first channel network 122, including an aperture 134 disposed entirely through, or optionally partially through the top substrate 106, whereby the signal from channel network 122 is only required to pass through the middle substrate 104 before it reaches the detector. An alternative structure is illustrated in FIG. 2, wherein the upper substrate layers are staggered to provide an unobstructed detection window for the channel networks disposed between the lower substrate layers.

In the case of optical detection, the detection system will typically include collection optics for gathering a light based signal transmitted through the detection window, and transmitting that signal to an appropriate light detector. Microscope objectives of varying power, field diameter, and focal length may be readily utilized as at least a portion of this optical train. The light detectors may be photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to the computer (described in greater detail below), via an AD/DA converter, for transmitting detected light data to the computer for analysis, storage and data manipulation.

In the case of fluorescent materials, the detector will typically include a light source which produces light at an appropriate wavelength for activating the fluorescent material, as well as optics for directing the light source through the detection window to the material contained in the channel or chamber. The light source may be any number of light sources that provides the appropriate wavelength, including lasers, laser diodes and LEDs. Other light sources may be required for other detection systems. For example, broad band light sources are typically used in light scattering/transmissivity detection schemes, and the like. Typically, light selection parameters are well known to those of skill in the art.

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an AD/DA converter as needed).

The computer typically includes appropriate software for receiving user instructions, either in the form of user input into a set parameter fields, e.g., in a GUI (graphical user interface), or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

III. Exemplary Applications

The multi-layer microfluidic devices described herein, have an extremely wide range of applications, including high throughput screening of chemical libraries in screening for lead compounds in drug discovery, nucleic acid analysis for genomic research, genetic testing and identification, and a myriad of other analytical operations.

One example of an application in which these multi-layer systems are particularly useful is in the performance of nucleic acid sequencing operations. For example, the multi-layer systems can be used to perform simultaneous sample preparation, separations and analysis for each of four separate sample treatments under either the Sanger or Maxam-Gilbert sequencing methods.

Figure 4:
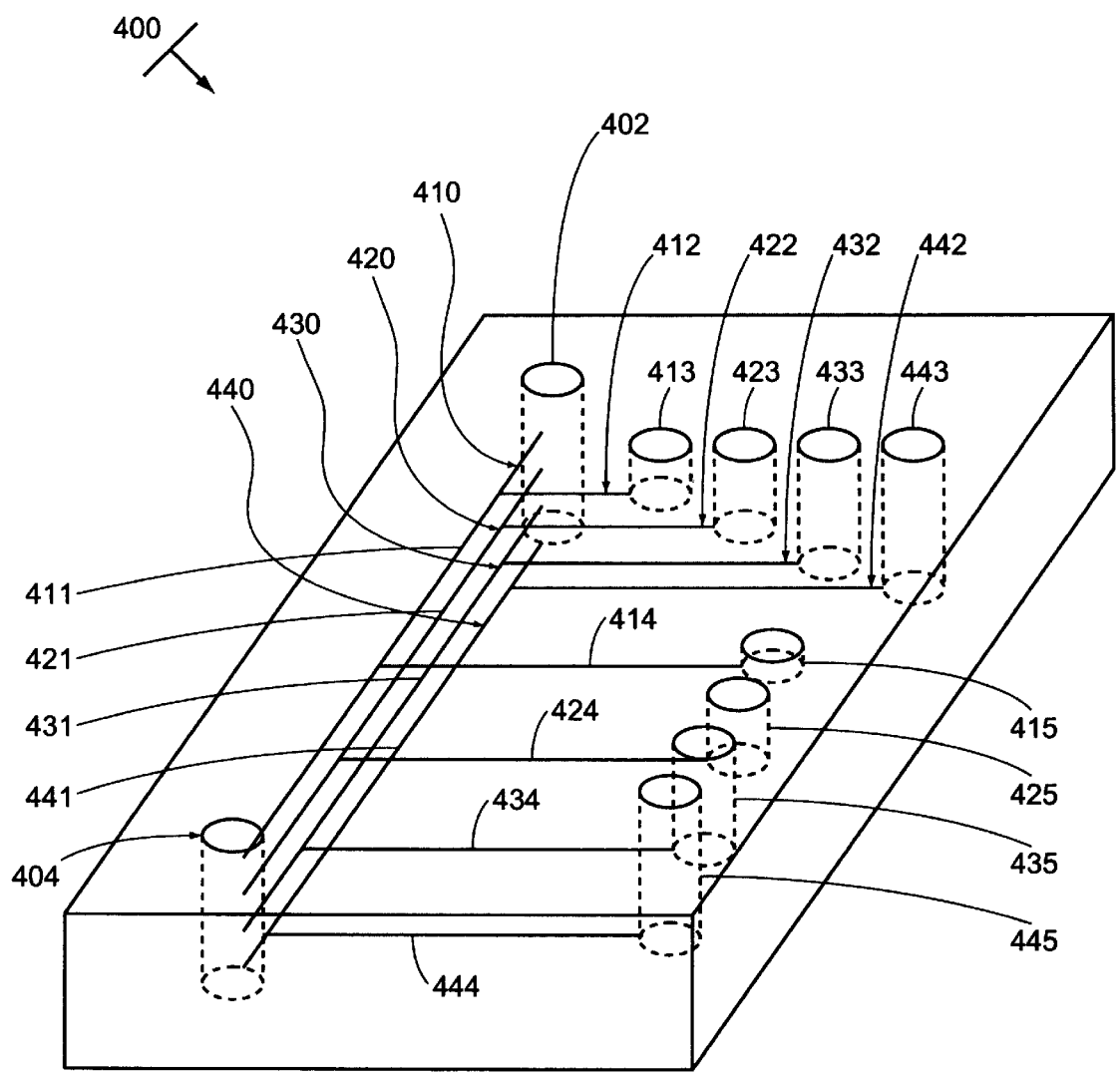
FIG. 4 illustrates a five-layer, four channel network device for carrying out four separate analyses on the same sample material simultaneously, e.g., nucleic acid sequencing.

In particular, with reference to the Sanger dideoxynucleotide sequencing process and FIG. 4, a single microfluidic device 400 includes four separate channel networks 410, 420, 430 and 440, each disposed in a separate layer of the device. Each of the channel networks includes a corresponding sample channel 411, 421, 431 and 441 in communication with a common sample port 402 and waste port 404. The sample containing the target nucleic acid that is to be sequenced, is deposited in the sample port 402, along with an effective concentration of DNA polymerase and primer sequence.

Each of the sample channels 411, 421, 431, and 441, is intersected by a corresponding second channel 412, 422, 432 and 442. Each of these channels leads to and is in fluid communication with a separate one of four different ports 413, 423, 433 and 443. In each of these ports is deposited a mixture of the four deoxynucleoside triphosphates (dNTPs:A; T; G; and C), as well as one of the four dideoxynucleoside triphosphates (ddNTPs: ddA, ddC; ddG; ddT), and other appropriate reagents, e.g., Mg++.

The sample is transported, simultaneously, along each of the four sample channels 411, 421, 431 and 441. The cocktail of dNTPs and the ddNTP is introduced into the channel at the intersection of the sample channel and the NTP channel, whereupon it mixes with the sample and begins extending the primer sequences along the length of the target sequence. For polymerase reactions requiring longer reaction times, e.g., for longer sequences, the sample channel can be elongated, or alternatively, widened in one region to provide a mixing/reaction chamber, to complete the polymerase reaction prior to separation of the reaction products. Similarly, flow rates are optionally slowed to allow more contact/mixing time between reagents.

The inclusion of the dideoxynucleotide results in the production of a nested set of nucleic acid polymerase products that terminates at the point the ddNTP was incorporated, indicating the complementary base in the target sequence, for that position. The mixture of reaction products is then transported across the intersection of the sample channel (411, 421, 431 or 441) and the corresponding separation channel (414, 424, 434, or 444, respectively) toward waste ports 415, 425, 435 and 445, respectively. The plug of reaction products present in the intersection is then electrophoresed down separation channel, separating the reaction products based upon size. Comparative analysis of the reaction product sizes in each different channel network permits the determination of the sequence. For additional complexity, different color detectable labels are incorporated in each of the separate reactions, to facilitate differentiation of signals from each channel network. However, single color detection is readily employed by providing for separate detection of separated reaction products in each of the four different reactions/channel networks, e.g., using detection windows disposed over each of the separation channels 415, 425, 435 or 445.

A similar device construction is used for performing degradative sequencing of nucleic acids, e.g., Maxam- Gilbert. In particular, instead of providing a different cocktail of dNTPs and ddNTP in each of the four ports 413, 423, 433 and 443, one merely deposits a different cleavage reagent, e.g., hydrazine or piperidine, or subjects the particular channel network to appropriate cleavage conditions, e.g., methylation and acid or base cleavage. See, e.g., Biochemistry by Lubert Stryer, (W. H. Freeman and Co.).

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A microfluidic system comprising:
    a body structure having at least first, second and third substrate layers, the second substrate layer disposed on top of the first substrate layer and the third substrate layer disposed on top cf the second substrate layer;
    at least first, second and third ports disposed in the body structure; at least first, and second microscale channel networks, the first channel network disposed between the first and second substrate layers, and being in fluid communication with the first and second ports, but not the third port, and the second channel network disposed between the second and third layers, and being in fluid communication with the first and third ports, but not the second port; and
    a material transport system operably linked to each of the first, second and third ports, for selectively controlling movement of material in the first and second channel networks, the material transport system comprises first, second and third electrodes in separate electrical contact with each of the first, second and third ports, respectively, and an electrical controller for concomitantly delivering a separate voltage to each of the first, second and third electrodes.

2. The system of claim 1, wherein the body structure further comprises a fourth substrate layer and a third channel network disposed between the third and fourth substrate layers.

3. The system of claim 1, wherein the body structure further comprises a fifth substrate layer and a fourth channel network disposed between the fourth and fifth substrate layers.

4. The system of claim 1, wherein each of the first and second channel networks comprises at least two intersecting microscale channels.

5. The system of claim 1, wherein at least one of the first and second channel networks comprises at least three intersecting channels.

6. The system of claim 1, further comprising a fourth port disposed in the body structure, the first and second channel networks being in fluid communication with the fourth port.

7. The system of claim 1, further comprising at least first and second detection windows, the first detection window disposed over a channel in the first channel network and the second detection window disposed over a channel in the second channel network.

8. The system of claim 1, wherein at least one channel of the first channel network and at least one channel of the second channel network comprise a separation matrix disposed therein.

9. The system of claim 1, wherein the first and second substrate layers each comprise a top and a bottom planar surface, and wherein the first channel network is microfabricated in the top surface of the first substrate layer, and the second channel network is fabricated in the top surface of the second substrate layer.

10. The system of claim 1, wherein the first and second substrate layers each comprise an upper and a lower planar surface, and wherein the first channel network is microfabricated in the bottom surface of the second substrate layer, and the second channel network is fabricated in the top surface of the second substrate layer.

11. The system of claim 1, wherein each of the first, second and third substrate layers is independently selected from the group of glass, silicon and polymeric substrates.

12. The microfluidic system of claim 1, wherein the material transport system comprises a pressure source for applying a pressure differential between the first port and the second and third ports.

13. The microfluidic system of claim 1, further comprising a detector in sensory communication with each of the first and second channel networks.

14. The microfluidic system of claim 12, wherein the microfluidic device further comprises an optical detection window disposed across each of the two channel networks for transmitting an optical signal from each of the two channel networks, and wherein the detector comprises an optical detector disposed adjacent to the detection window for receiving the optical signal.

15. The microfluidic system of claim 1, comprising a sample material disposed in the first port, a first reactant disposed in the second port and a second reactant disposed in the third port.

16. A microfluidic device comprising:
    a body structure comprising at least first, second and third substrate layers wherein the second substrate layer comprises an upper planar surface and a lower planar surface, the second substrate layer disposed on top of the first substrate layer and the third substrate layer disposed on top of the second substrate layer;
    at least first and second microscale channel networks, the first channel network disposed between the first and second substrate layers, and the second channel network disposed between the second and third layers, wherein the first channel network is microfabricated in the bottom surface of the second substrate layer, and the second channel network is fabricated in the top surface of the second substrate layer; and
    at least one fluid passage disposed through the second substrate layer providing fluid communication between the first channel network and the second channel network.

17. A microfluidic device, comprising:
    a body structure comprising first, second and third planar substrates, each of the substrates having upper and lower planar surfaces, wherein the upper surface of the first substrate is mated with the lower surface of the second substrate and the upper surface of the second substrate is mated with the lower surface of the third substrate, and a first and second ports disposed through the second and third substrates, and a third port disposed through the third substrate;
    a first channel network having at least first and second termini, the first channel network defined between the upper surface of the first substrate and the lower surface of the second substrate, the first channel network being in fluid communication with the first port at a first terminus of the first channel network and in fluid communication with the second port at a second terminus of the first channel network; and a second channel network having at least first and second termini, the second channel network defined between the upper surface of the second substrate and the lower surface of the third substrate, the second channel network in fluid communication with the first port at the first terminus of the second channel network and in fluid communication with the third port at the second terminus of the second channel network.

18. A method of performing a plurality of different analyses on a single fluid sample, the method comprising:

providing a microfluidic device having a body structure comprising at least first, second and third substrate layers, the second substrate layer disposed on top of the first substrate layer and the third substrate layer disposed on top of the second substrate layer, and at least first and second microscale channel networks, the first channel network disposed between the first and second substrate layers, and being in fluid communication with first and second ports disposed in the body structure, and the second channel network disposed between the second and third layers, and being in fluid communication with the first port and a third port disposed in the body structure;

placing the fluid sample into the first port;

transporting the fluid sample through each of the first and second channel networks, each of the channel networks performing a different reaction on the fluid sample;

detecting a result of the reaction performed in each of the two channel networks.

19. A microfluidic device for sequencing a target nucleic acid, comprising:

a body structure comprising at least five substrate layers, four separation channels, each of the separation channels disposed between two different substrate layers;

a common sample reservoir connected to each of the four separation channels via four separate sample introduction channels;

four reagent channels, each reagent channel independently connecting each of the four sample introduction channels with a separate one of four separate reagent reservoirs disposed in the body structure, each of the four separate reagent reservoirs comprising a separate dideoxynucleotide disposed therein.

20. A microfluidic device for sequencing a target nucleic acid, comprising:

a body structure having at least first, second, third, fourth and fifth substrate layers, the second substrate layer disposed on top of the first substrate layer, the third substrate layer disposed on top of the second substrate layer, the fourth substrate layer disposed on top of the third substrate layer and the fifth substrate layer being disposed on top of the fourth substrate layer;

a first channel network disposed between the first substrate layer and the second substrate layer, the first channel network comprising a first channel connecting a first and a second reservoir disposed in the body structure, a first reagent channel connecting a third reservoir disposed in the body structure with the first channel between the first reservoir and the second reservoir, and a first separation channel connecting the first channel between the first reagent channel and the second reservoir;

a second channel network disposed between the second substrate layer and the third substrate layer, the second channel network comprising a second channel connecting the first and second reservoirs, a second reagent channel connecting a fourth reservoir disposed in the body structure with the second channel between the first and second reservoirs, and a second separation channel connecting a fifth reservoir with the second channel between the second reagent channel and the second reservoir;

a third channel network disposed between the third substrate layer and the fourth substrate layer, the third channel network comprising a third channel connecting the first and second reservoirs, a third reagent channel connecting a sixth reservoir with the third channel between the first and second reservoirs, and a third separation channel connecting a seventh reservoir with the third channel between the third reagent channel and the second reservoir;

a fourth channel network disposed between the fourth substrate layer and the fifth substrate layer, the fourth channel network comprising a fourth channel connecting the first and second reservoirs, a fourth reagent channel connecting an eighth reservoir disposed in the body structure with the fourth channel between the first and second reservoirs, and a fourth separation channel connecting a ninth reservoir disposed in the body structure, with the fourth channel between the fourth reagent channel and the second reservoir.

21. A method of sequencing a target nucleic acid, comprising:

providing microfluidic device having a body structure that comprises at least five substrate layers, at least four separation channels, each of the separation channels disposed between two different substrate layers, a common sample reservoir having a fluid sample containing the target nucleic acid disposed therein, the sample reservoir connected to each of the four separation channels via four separate sample introduction channels, and four reagent channels, each reagent channel independently connecting each of the four sample introduction channels with a separate one of four separate reagent reservoirs disposed in the body structure, each of the four separate reagent reservoirs containing a separate one of four reagent mixtures, each reagent mixture including four different nucleoside triphosphates, primer sequences complementary to the target nucleic acid sequence, and, a nucleic acid polymerase enzyme, and a separate dideoxynucleoside triphosphate;

separately combining the target nucleic acid with each of the four reagent mixtures in each of the four sample introduction channels;

sizing products of the combining step from each of the four sample introduction channels in each of the four separation channels, respectively; and determining the sequence of the target nucleic acid from the size of the pro ducts as determined in the sizing step.

22. The device of claim 16, wherein each of the first and second channel networks comprises at least two intersecting microscale channels.

23. The device of claim 16, wherein at least one of the first and second channel networks comprises at least three intersecting channels.

24. The device of claim 16, further comprising at least a first detection window disposed over a channel in at least one of the first and second channel networks.

25. The device of claim 24, wherein the first detection window is disposed over a channel in each of the first and second channel networks.

26. The device of claim 24, further comprising at least a second detection window, the first detection window being disposed over a channel in the first channel network and the second detection window being disposed over a channel in the second channel network.

27. The device of claim 16, further comprising at least first and second ports disposed in the body structure, each of the first and second ports being in fluid communication with at least one of the first and second channel networks.

28. The device of claim 27, wherein the first and second ports are in fluid communication with the first channel network.

29. The device of claim 27, wherein the first port is in fluid communication with the first channel network and the second port is in fluid communication with the second channel network.

30. The device of claim 27, further comprising at least a third port disposed in the body structure, the third port being in fluid communication with at least one of the first and second channel networks.

31. The device of claim 16, wherein at least one channel in the first or second channel network comprises a separation matrix disposed therein.

32. The device of claim 16, wherein each of the first, second and third substrate layers is independently selected from glass, quartz, silicon, and polymeric substrates.

33. The device of claim 16, wherein each of the first, second and third substrate layers comprises glass or quartz.

34. The device of claim 16, wherein each of the first, second and third substrate layers comprises a polymeric substrate selected from polymethylmethacrylate (PMMA), polycarbonate, polytetrafluoroethylene, polyvinylchloride (PVC), polydimethylsiloxane (PDMS), and polysulfone.

35. The microfluidic device of claim 27, further comprising a material transport system operably linked to at least one of the first and second ports, for controlling movement of material in the first and second channel networks.

36. The microfluidic device of claim 35, wherein the material transport system comprises at least first and second electrodes in separate electrical contact with each of the first and second ports, respectively, and an electrical controller for delivering a separate voltage to each of the first and second electrodes.

37. The device of claim 35, wherein the material transport system comprises a pressure source for applying a pressure differential between the first and second ports.

38. The device of claim 16, further comprising a detector in sensory communication with at least one of the first and second channel networks.

39. The device of claim 16, further comprising a sample fluid disposed in the first port, and at least a first reactant disposed in the second port.

* * * * *

UNITED STATES PATENT AND TRADEMARK OFFICE
CERTIFICATE OF CORRECTION

PATENT NO.   : 6,167,910 B1
DATED        : January 2, 2001
INVENTOR(S)  : Chow

It is certified that error appears in the above-identified patent and that said Letters Patent is hereby corrected as shown below:

Column 15,
Line 21, please delete "cf" and insert -- of --.
Line 23, after "first" please delete ",".

Column 16,
Line 21, please delete "12" and insert -- 1 --.

Column 18,
Line 57, please delete "pro ducts" and insert -- products --.

Signed and Sealed this

Twenty-third Day of October, 2001

Attest:

NICHOLAS P. GODICI
Acting Director of the United States Patent and Trademark Office Attesting Officer